United States Patent
Kelly et al.

(10) Patent No.: US 7,295,872 B2
(45) Date of Patent: Nov. 13, 2007

(54) SYSTEM FOR AND METHOD OF POWER EFFICIENT ELECTRICAL TISSUE STIMULATION

(75) Inventors: Shawn Kelly, Cambridge, MA (US); Joseph Rizzo, Boston, MA (US); John Wyatt, Sudbury, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 669 days.

(21) Appl. No.: 10/267,764

(22) Filed: Oct. 9, 2002

(65) Prior Publication Data

US 2003/0130699 A1 Jul. 10, 2003

Related U.S. Application Data

(60) Provisional application No. 60/328,346, filed on Oct. 10, 2001.

(51) Int. Cl.
*A61N 1/18* (2006.01)
(52) U.S. Cl. ............ 607/2; 607/4; 607/9; 607/34; 607/53; 607/61
(58) Field of Classification Search ............ 607/34, 607/36, 33, 61, 2, 4–5, 9, 13, 53
See application file for complete search history.

(56) References Cited

U.S. PATENT DOCUMENTS

| | | | |
|---|---|---|---|
| 4,082,097 A | 4/1978 | Mann et al. | |
| 4,114,627 A | 9/1978 | Lewyn et al. | |
| 4,399,818 A | 8/1983 | Money | |
| 4,596,252 A * | 6/1986 | Nelson | 607/9 |
| 4,628,933 A * | 12/1986 | Michelson | 607/53 |
| 5,312,439 A | 5/1994 | Loeb | |
| 5,522,865 A | 6/1996 | Schulman et al. | |
| 5,876,425 A | 3/1999 | Gord et al. | |
| 6,035,237 A | 3/2000 | Schulman et al. | |
| 6,181,969 B1 | 1/2001 | Gord et al. | |
| 6,415,186 B1 | 7/2002 | Chim et al. | |
| 2002/0068957 A1 | 6/2002 | Wolfe et al. | |

OTHER PUBLICATIONS

"A Neuro-Stimulus Chip with Telemetry Unit for Retinal Prosthetic Device" by Liu, et al., IEEE Journal of Solid-State Circuits, vol. 35, No. 10, Oct. 2000.
WIPO Publication No. WO 03/030991 A1 entitled "Power Saving System for Neural Implant Devices" by Wyatt, et al., dated Apr. 17, 2003.
International Search Report Re: PCT/US02/32509, filed Oct. 10, 2002.

* cited by examiner

*Primary Examiner*—Robert Pezzuto
*Assistant Examiner*—Shevon Johnson
(74) *Attorney, Agent, or Firm*—Sam Pasternack; Choate Hall & Stewart LLP

(57) ABSTRACT

Circuitry for and method of power efficient operation of, and energy recovery from, tissue-stimulating electrodes having high charge capacities. Post-stimulation energy is recovered from the electrodes through a variety of techniques into circuit elements such as other electrodes, an intermediate distribution system, a power supply or any other elements, through the use of sequential switching. Energy is also recoverable from the intermediate distribution system, which preferably is comprised of one or more storage capacitors operating a different voltages. Efficient power transfer among circuit elements is effected by transferring energy while limiting element-element voltage differences and/or voltage differences between the elements and the capacitances of the electrodes.

3 Claims, 11 Drawing Sheets

SYSTEM FOR AND METHOD OF POWER EFFICIENT ELECTRICAL TISSUE STIMULATION

This application claims the benefit of priority to U.S. Provisional Application No. 60/328,346 filed Oct. 10, 2001.

FIELD OF THE INVENTION

The present invention relates to the field of medical devices, and more particularly relates to medical devices capable of generation of tissue or nerve stimulating pulses. Even more particularly, the present invention relates to efficient power utilization in, and energy recovery from, electrodes of implantable prostheses, such as retinal or cochlear stimulators.

BACKGROUND OF THE INVENTION

Devices for electrically stimulating tissue, including cochlear implants, pacemakers, muscle and spinal cord stimulators, have been in use for decades. Retinal prostheses that might assist some of the estimated 10 million people worldwide who are blind as a result of degenerative retinal diseases, such as age-related macular degeneration and retinitis pigmentosa, are under development based on the concept of replacing photoreceptor function with an electronic nerve-stimulating device.

Many tissue-stimulating prostheses provide electrical signals to an implanted section, which then generates excitation signals to excite the tissue of a patient by means of appropriately positioned stimulation electrodes or arrays of electrodes. Common in some tissue stimulators is a two-part design, wherein an external section transmits RF energy that is inductively coupled by a transcutaneous RF link to the implanted section. The energy of the coupled RF electrical signals is rectified and stored by a power supply located in the internal section. It is that power supply that provides the energy required to power the internal section and to generate the stimulus signals.

To increase patient safety, to minimize the power requirements of a tissue stimulator, and because power dissipation losses are in proportion to the square of the voltage, it is desirable to operate the tissue stimulator at low voltages that are no greater than required. This is especially true in implantable stimulator electronics. During stimulation, the electrodes of tissue stimulating devices are typically driven by a constant current source to a prescribed level of charge, resulting in storage of that charge, and therefore storage of energy, within the electrodes. To ensure charge balancing to avoid electroplating the electrodes, the same amount of charge is then driven in the opposite direction (changing polarity) until the electrodes are left uncharged. Typical circuit techniques are very inefficient when driving this type of electrode, often using more than twice the necessary energy during the first phase of current drive, and even more during the second phase.

U.S. Pat. No. 5,522,865 to Schulman, et al., entitled "Voltage/Current Control System for a Human Tissue Stimulator" discloses a human tissue stimulating system that comprises an audio responsive system for artificially stimulating a cochlea to improve hearing for the hearing impaired. The implanted stimulator includes a power supply that extracts raw power from a data signal, a voltage downconverter for providing a number of output voltages from the extracted raw power signal, and a storage capacitor that serves as the power source for portions of the stimulator. One of the output voltages is applied to isolated refresh voltage capacitors, where it controls a voltage controlled current source that supplies output to the electrodes through a complex switch matrix. Energy is conserved by turning off and on various subsystems within a control processor, and by optimizing power dissipation of a conventional input switching regulator by controlling the RF power transmitted from an external source to the implanted stimulator based on a telemetered voltage drop across the regulator, indicating what power is required to be transmitted for just sufficient stimulator operation.

U.S. Pat. No. 5,876,425 to Gord, et al., entitled "Power Control Loop for Implantable Tissue Stimulator" also describes a feedback power control loop utilizing back telemetry from the implantable device. The voltage level of a tank capacitor utilized as an internal rechargeable power source is transmitted to an external power supply processor for computation and delivery of an appropriate amount of power to maintain normal operation, while minimizing transmission of extra energy that might otherwise be dissipated.

U.S. Pat. No. 6,415,186 to Siu-Chor Chim, et al., entitled "Active Feed Forward Power Control Loop" discloses a feed forward power control loop for providing power to the implanted part of a tissue stimulator. Power consumption is similarly kept low by transmitting across a wireless transcutaneous transmission link only the amount of power required by the implanted device, as predicted by the power control loop processor. The reference discloses the use of intermittent telemetry and predictive modeling to determine the appropriate amount of power to transmit.

Each of the references cited above approaches power transfer optimization by using tank capacitor voltage telemetry to determine power transmission. They address power consumption efficiency of the implanted circuitry, to a greater or lesser extent, by turning on and off circuit components, and otherwise treat conventionally the transfer of energy from the power supply to the electrodes. None address recovering energy from the electrodes and other components after stimulation has occurred.

U.S. Pat. No. 6,181,969 to Gord, entitled "Programmable Current Output Stimulus Stage for Implantable Device" discloses a programmable output current source for use within an implantable tissue or nerve stimulator. Each electrode node has parallel-connected P-FET current source sets permanently connected between it and a positive voltage rail, and parallel-connected N-FET current source sets permanently connected between it and a negative voltage rail. The higher power requirement of the PFET and NFET current sources is kept to a minimum by avoiding physically or electrically "switching" the electrode nodes between one or more circuit locations, or to different sides of a current or voltage source so as to change the polarity of the current flowing through the node. Rather, the P-FET sources "source" current to the node, and the N-FET sources receive, or "sink", current from the node. Such a non-switching approach is achieved at the cost of more circuit components.

Accordingly, there is a continuing need for greater power utilization and delivery efficiency in tissue stimulating devices. The present invention satisfies such needs.

SUMMARY OF THE INVENTION

The present invention provides a variety of circuits and techniques for power-efficient operation of, and energy recovery from, tissue-stimulating electrodes. The invention takes advantage of recent advances in electrical properties of the electrodes to reduce the power required for effective stimulation.

The present invention finds particular relevance with implantable tissue stimulators, wherein optimal power efficiency can prolong the life of the device and decrease the risk of patient harm. The use of iridium oxide and other types of electrodes that have vastly higher charge-capacity properties than platinum or other electrode materials used in the past makes the present invention feasible. The principles of the systems and methods described below are applicable to any tissue stimulation device (e.g., retinal and cochlear implants, cortical stimulator, spinal stimulator, cardiac pacemaker, etc.) employing electrodes having a series capacitance.

As used herein, the term "power supply" refers to the portion of a tissue stimulator responsible for, in the case of an implanted stimulator, receiving energy from an external power-transmitting unit and at least temporarily storing the energy for use by other portions of the stimulator for generating electrical stimulation signals. The power supply employed is dependent upon the nature of the tissue stimulator. In a retinal stimulator, for example, the power supply may comprise a secondary coil for coupling AC magnetic fields transmitted from outside the patient's body. In larger tissue stimulators, the power supply may comprise a battery.

In one aspect, the present invention provides systems and methods for recovering energy from tissue stimulating electrodes post-stimulation. As discussed in the previous section, this energy has, in the past, been wasted. As will be described below, there is residual energy in the capacitance of post-stimulated electrodes. The recovered energy may be utilized in driving one or more other electrodes to be used in subsequent stimulation. In other embodiments, the recovered energy is transferred to other circuit elements within the tissue stimulator In another aspect, the present invention provides systems and methods for the efficient transfer of energy within a tissue stimulator.

In one embodiment, a system in accordance with the invention includes one or more tissue stimulating electrodes, a power supply, and transfer circuitry coupled to the power supply and the electrodes that provides energy to the electrodes directly from the power supply while limiting voltage differences between the power supply and the capacitance of the electrodes to which the power supply is to be connected. The transfer circuitry may also operate so as to remove energy from one or more previously stimulated electrodes and return the energy directly or indirectly to the power supply.

In another embodiment, the system may have an intermediate distribution system (IDS) disposed between the electrodes and the power supply. The IDS provides one or more voltage sources to the electrodes to be driven, and may be fed from the power supply through power transfer circuitry. The power transfer circuitry maintains the voltage sources at the desired, preferably DC, voltages by providing energy from the power supply while limiting voltage differences between the power supply and the voltage sources to which the power supply is to be connected. In certain embodiments, the power transfer circuitry may include a synchronous switching rectifier for directly supplying power to or recovering power from the voltage sources. A switching network provides energy to the electrodes from the voltage sources while limiting voltage differences between the voltage sources and the capacitance of the electrodes to which the voltage sources are to be connected.

In certain embodiments, the IDS is comprised of a plurality of storage capacitors among which one or more electrodes, or groups of electrodes, are appropriately switched. Single capacitor embodiments of the IDS are also possible by driving a constant current into a single capacitor via the power transfer circuitry, thereby creating a psuedo-ramping voltage source. This ramping capacitor is connected to the electrodes during a single constant-current phase. There will be some ripple in the voltage ramp, but it can be limited.

In another embodiment, a system for power-recovery in a tissue stimulator comprises one or more previously stimulated electrodes, one or more elements into which energy from the one or more previously stimulated electrodes will be recovered, and a switching network that provides sequential connections from the one or more previously stimulated electrodes to the one or more elements. The one or more elements are preferably electrodes to be used in subsequent stimulation, or groups thereof, but could be any electrical element capable of utilizing the recovered energy. The electrodes to be used in subsequent stimulation may be completely uncharged prior to energy transfer, but, as will be described below, optimal energy efficiency is achieved through a method of partially pre-charging the electrodes that will be transferred the recovered energy.

The system components described above may be designed to operate based on pre-set timing intervals. Alternatively, they may be responsive to monitored electrical parameters of the system. For example, the power transfer circuitry may be responsive to the difference between the voltage of the capacitance of the previously stimulated electrodes and the voltage of the power supply. Or, the switching network may be responsive to the difference between the voltage(s) of the capacitances of the previously stimulated electrodes and the voltage(s) of the voltage sources to which the previously stimulated electrodes are to be connected, or between the capacitances of the previously-stimulated electrodes and the capacitances of uncharged and/or partially charged electrodes to be stimulated.

In preferred embodiments, the switching network provides sequential connections from one or more storage capacitors (of an IDS) to one or more of the electrodes to be stimulated while limiting voltage differences between the storage capacitors and the capacitances of the one or more electrodes to which the one or more storage capacitors are to be connected. A judicious selection of connection sequences results in progressive addition to or removal of energy from the capacitances of the electrodes being connected.

DETAILED DESCRIPTION OF CERTAIN PREFERRED EMBODIMENTS OF THE INVENTION

Figure 1:
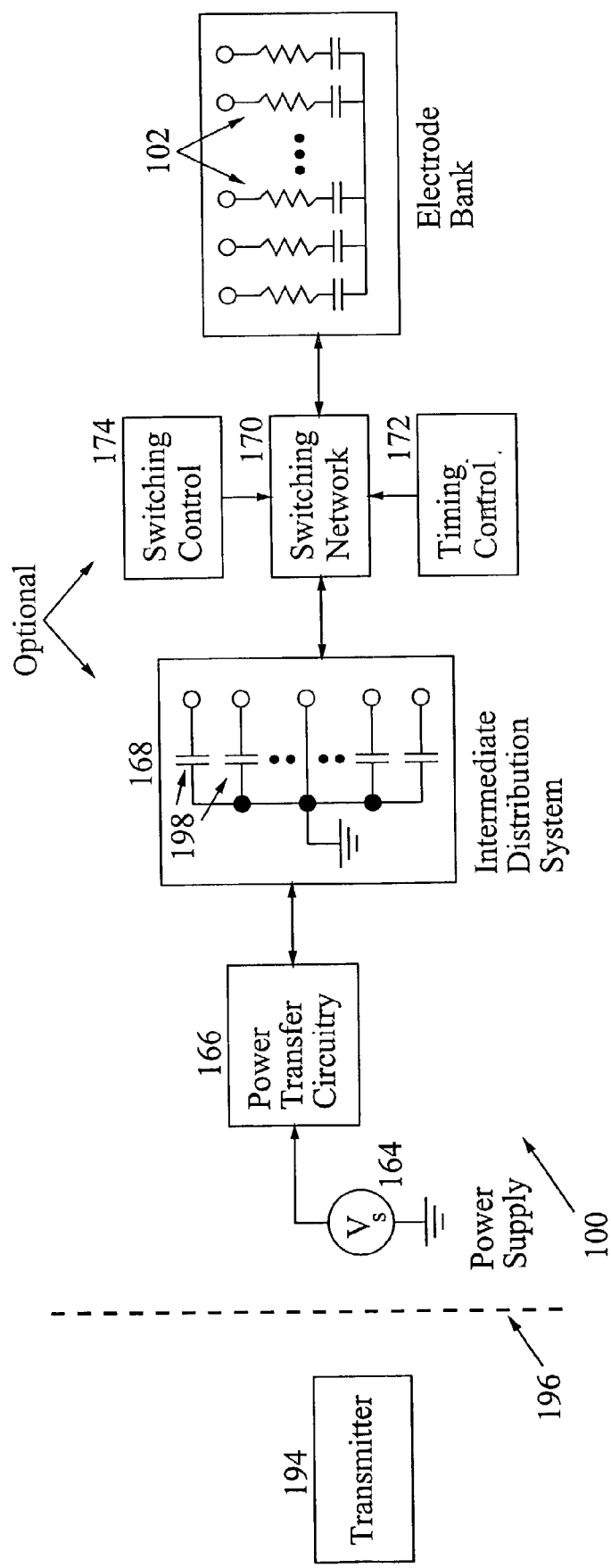
FIG. 1 is an electrical schematic of a power-efficient energy transfer system in accordance with the invention.

Preferred embodiments of the invention will now be described with reference to the accompanying drawings. The circuitry shown in the drawings and described below is simplified in that not all of the components utilized in the system are shown, but sufficient components are shown to clearly teach the novel aspects of the present invention.

The present invention provides a variety of circuits and techniques for power-efficient operation of, and energy recovery from, tissue-stimulating electrodes. The invention takes advantage of recent advances in electrical properties of the electrodes to reduce the power required for effective stimulation.

Electrodes

Figure 2:
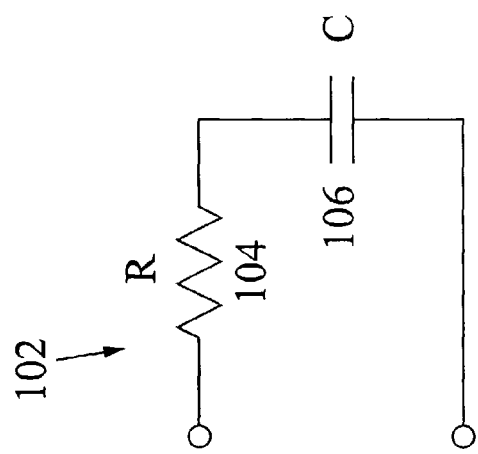
FIG. 2 is an electrical schematic diagram of circuit equivalent model of a tissue stimulating electrode.

With reference to FIG. 1, the present invention provides a system 100 for efficient energy transfer in a tissue stimulator utilizing one or more tissue stimulating electrodes 102. The electrodes 102 are preferably manufactured from oxidized iridium or other material with a high charge capacity. Fabrication of the electrodes can be performed using any techniques known to those skilled in the art, such as electrodeposition or infusion of molten metal under pressure. In a preferred embodiment of a retinal tissue stimulator employing the systems and methods in accordance with the present invention, the electrodes used may include 400 um diameter iridium oxide electrodes. As shown in FIG. 2, each of the electrodes 102 can be modeled as a modest resistive element 104 (about 1 KOhm) in series with a very large capacitance 106 (300 nF to 3 uF, depending on the oxidation process). This simple model has some limitations (a significant conducting path in parallel with the capacitance forms at high enough voltage), and is not exact, but is sufficient for modeling the response to currents and voltages typically seen during tissue stimulation.

Figure 3A:
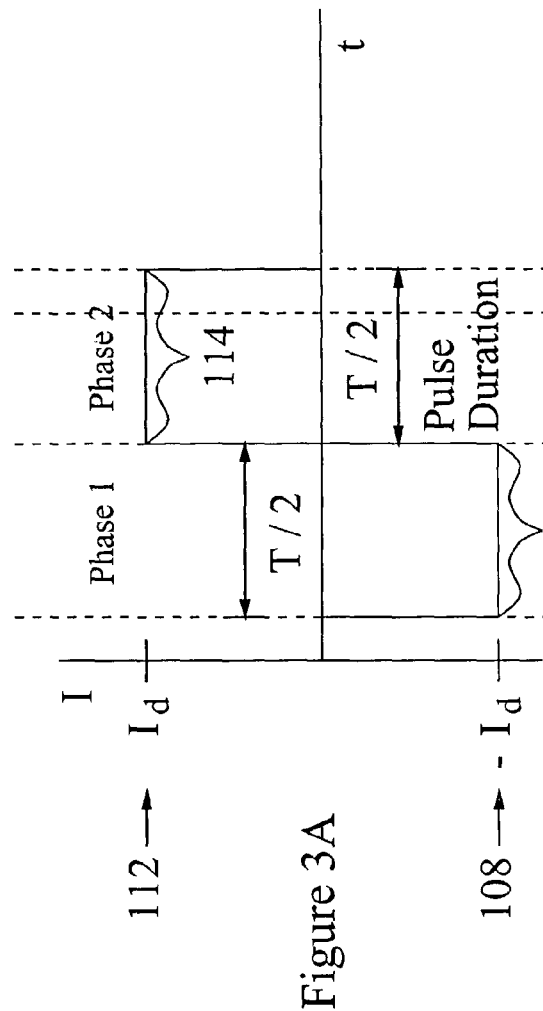
FIGS. 3A, 3B are plots of ideal constant current and associated voltage waveforms for optimally driving a tissue stimulating electrode.

The usual method of stimulation, as shown in FIG. 3A and discussed in further detail below, is a constant current drive $-I_d$ 108 for a fixed time T/2 110. This deposits a charge on the capacitance 106 of electrode 102, resulting in a voltage across the electrode and stimulation of the nerve or muscle tissue near the electrode. If left open-circuited for typical times of interest (several milliseconds or tens of milliseconds), the charge of the capacitance 106 will not leak off electrode 102, and can be thought of as stored energy. The process is then reversed by driving an opposite current $+I_d$ 112 through electrode 102 for the same time T/2 114, leaving electrode 102 uncharged and ready for the next stimulation.

Basic Method of Energy Recycling

Figure 4:
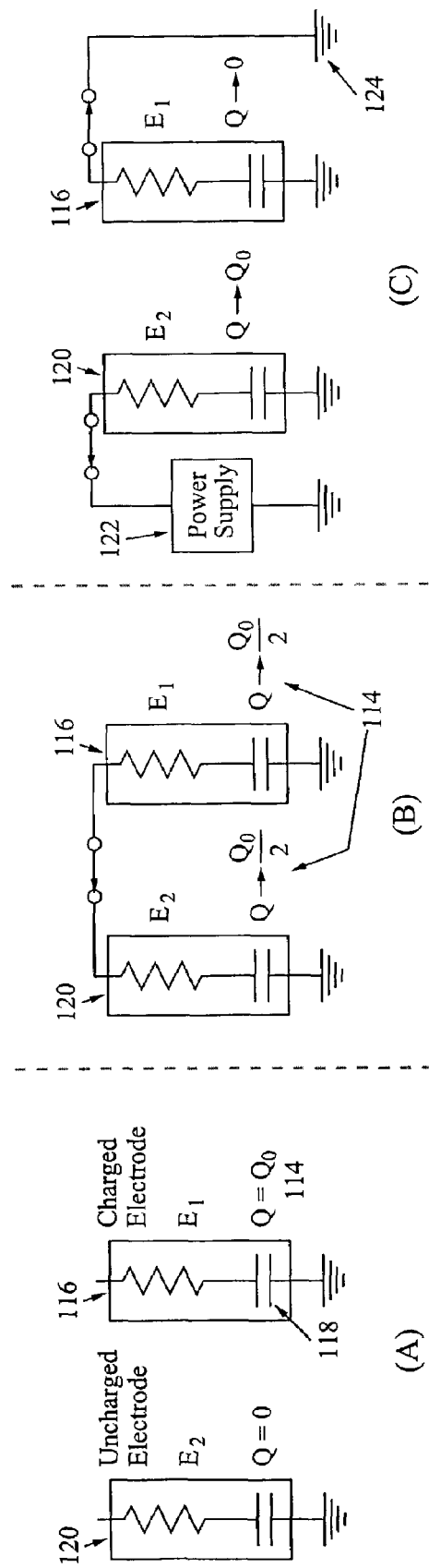
FIG. 4 is an electrical schematic diagram of a simple circuit segment illustrating the concept of charge sharing between a charged electrode and an uncharged electrode.

As shown in FIG. 4A, after a charge $Q_0$ 114 has been driven onto an electrode $E_1$ 116, resulting in stimulation of adjacent tissue, that electrode's capacitance 118 contains stored energy. Furthermore, the charge $Q_0$ 114 on electrode $E_1$ 116 must be removed to prevent electroplating and to prepare for future stimulations. The simplest method for energy recycling, as shown in FIG. 4B, involves connecting charged electrode $E_1$ 116 to an uncharged electrode $E_2$ 120, allowing them to share charge $Q_0$ 114. In a final step, as shown in FIG. 4C, electrode $E_1$ 116 is shorted to ground 124 to continue its discharge, while $E_2$ 120 is fully charged by some type of supply source 122. More complicated procedures increase the efficiency of this technique.

More Efficient Charge Recycling

Figure 5A:
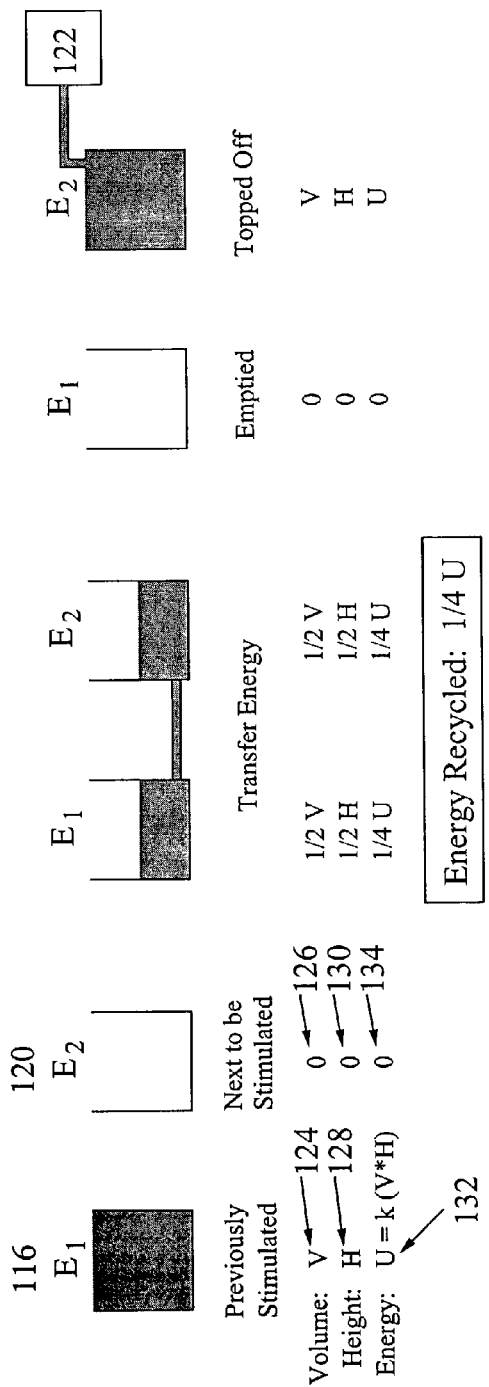
FIGS. 5A, 5B are illustrations provided for the purpose of analogizing electrode charge states to the volume of water in hypothetical water buckets.
Figure 5B:

FIGS. 5A and 5B are useful in visualizing the electrodes $E_1$ 116, $E_2$ 120 as buckets of water, wherein the charges of their capacitances are equivalent to one or more volumes 124, 126 of water, their voltages are equivalent to the heights 128, 130 of the water volumes, and their energies are proportional to the products 132, 134 of the two. FIG. 5A illustrates the simple recycling scheme, while FIG. 5B shows a more efficient scheme involving partially pre-filling the empty bucket (i.e., partially pre-charging electrode $E_2$ 120). As can be seen, one drawback of the simple method is its inefficiency. Assuming that the RC time constant of electrode $E_1$ 116 is much shorter than the time t that the electrodes are connected, half the charge V 124 will be transferred to electrode $E_2$ 120, giving it half the voltage H 128 originally on the electrode $E_1$ 116. But since the energy stored on a capacitor is proportional to the product of charge and voltage, electrode $E_2$ 120 now has only ¼ of the energy U 132 originally stored on $E_1$ 116, and the other ¾ of the required energy must be supplied by the supply source 122.

In FIG. 5B, a more efficient way to transfer charge between the two electrodes $E_1$ 116', $E_2$ 120' is demonstrated. The unstimulated electrode $E_2$ 120' is partially pre-charged, then connected to previously stimulated electrode $E_1$ 116', and finally driven by supply source 122 to complete the required charge. This method can recover as much as ⅓ of the energy U 136 from the previously stimulated electrode $E_1$ 116'. More energy can additionally be recovered by connecting the uncharged electrode $E_2$ 120 to a series of previously stimulated electrodes, but the complexity of control circuitry required grows significantly and the charging times required would limit stimulation frequencies that could be utilized.

In a direct electrode-to-electrode transfer, at best ⅓ of the energy can be recovered because the electrodes are at such different voltages when they are shorted together. This means that a large voltage develops across the electrode resistances, burning power. This drawback leads to a more sophisticated way of recovering energy from the electrodes, and an optimal method of delivering energy to them.

Response of Electrodes to Drive Current

Figure 3B:
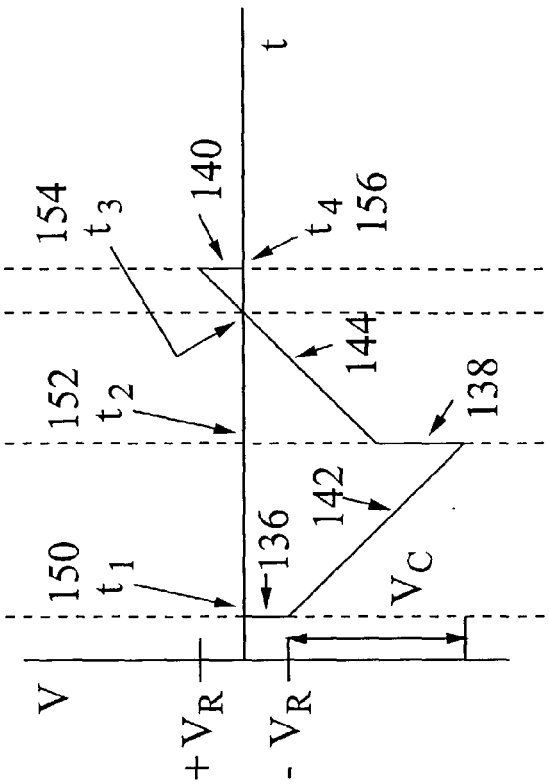

FIG. 3B shows the voltage waveform across any tissue stimulating electrode 102 in response to the constant current drives 108, 112 with a negative pulse during the first phase T/2 110, a typical configuration. The resistive element 104 of electrode 102 is responsible for the steps (136, 138, 140) in the voltage waveform, and the capacitance 106 of electrode 102 is responsible for the ramps (142, 144).

The first voltage step 136 and last voltage step 140 in the waveform shown have magnitude $$V_R = I_d R \qquad \text{Eq. 1}$$

The middle voltage step 138 is twice that value, since the change in drive current at that moment is twice the magnitude. The magnitude of each ramp segment 142, 144 is $$V_C = \frac{Q}{C} = \frac{I_d T}{2C} \qquad \text{Eq. 2}$$

The power into the electrode at any moment in time is $$P(t) = I(t)V(t) \qquad \text{Eq. 3}$$

In the first phase T/2 110, the product of the negative current $-I_d$ and the negative voltage is positive power into electrode 102. The energy into electrode 102 during the first phase T/2 110 (between $t_1$ 150 and $t_2$ 152), $U_1$, is the integral of the power over time T, or the product of the constant current Id and the area under the voltage waveform:

$$U_1 = \int_0^T P(t)dt \qquad \text{Eq. 4}$$
$$= (-I_d)\left(-\frac{T}{2}V_R - \frac{1}{2}\frac{T}{2}V_C\right)$$
$$= I_d^2 \left(\frac{RT}{2} + \frac{T^2}{8C}\right)$$

The energy into the resistive element 104 of electrode 102 is lost to heat, but the energy into the capacitance 106 is stored, and potentially recoverable. During the second phase T/2 114 (between $t_2$ 152 and $t_4$ 156), some of this stored capacitive energy is lost in the resistance, but some is returned from electrode 102, as illustrated in FIG. 3B.

Note that for a short time, between $t_2$ 152 and $t_3$ 154, the current is positive but the voltage is negative, meaning the power into electrode 102 is negative. Put another way, the electrode is "supplying power". In traditional systems, this power is not recovered into the supply where it may be used again. Rather, it is burned in the current source circuitry. The present invention recovers and reuses some of that returned energy.

The total energy into electrode 102 during the second phase T/2 114 (between $t_2$ 152 and $t_4$ 156) is calculated in the same way as in Eq. 4, and is:

$$U_2 = (I_d)\left(\frac{T}{2}V_R - \frac{1}{2}\frac{T}{2}V_C\right) = I_d^2\left(\frac{RT}{2} - \frac{T^2}{8C}\right) \qquad \text{Eq. 5}$$

The returned energy can be seen in the negative sign in Eq. 5. The total energy into electrode 102 over both phases 110, 114 is $$U_{Tot} = U_1 + U_2 = I_d^2 RT \qquad \text{Eq. 6}$$

This is the familiar power relation for a resistor, $P = I^2 R$, integrated over the total biphasic pulse time T. In other words, the capacitance 106 of electrode 102 does not burn any power, it merely stores energy and then returns it.

Conditions for Energy Recovery

As stated above, the capacitance 106 of electrode 102 cannot burn power. It merely stores the energy, to be returned during the second phase 114. The energy is in the form of electric charge held at an electric potential (voltage). When the charge is removed from the capacitance 106 during the second phase 114, it necessarily passes through the resistive element 104, which burns power, converting some of the energy to heat. The degree to which this occurs determines whether usable energy may be recovered from the capacitive part of the electrode.

Figure 6B:
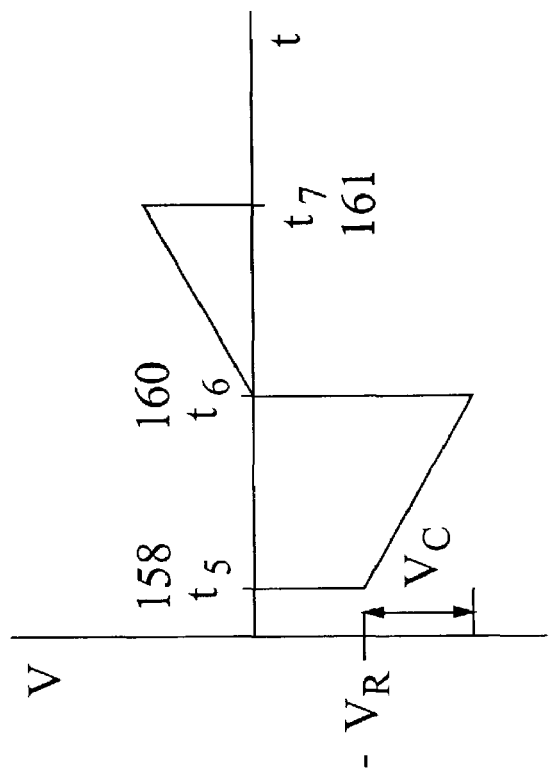
FIGS. 6A, 6B are plots of electrode voltage waveforms demonstrating recoverable and non-recoverable post-stimulation energy.
Figure 6A:
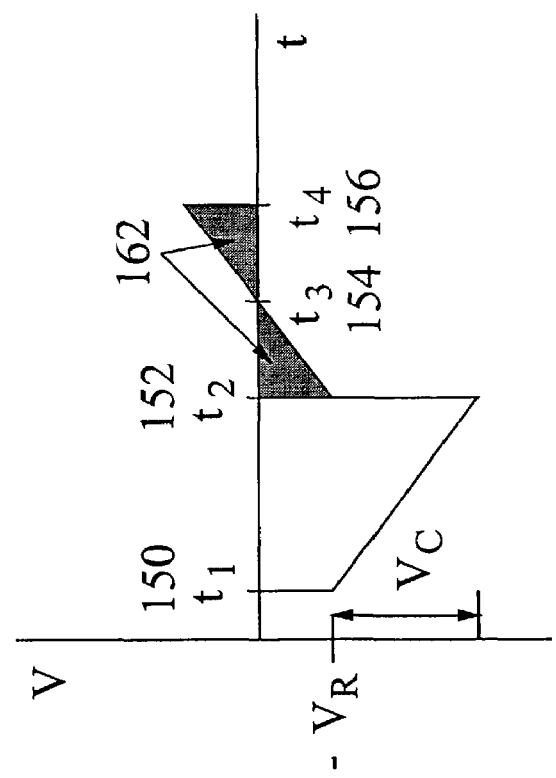

FIGS. 6A, 6B show two illustrative cases of the voltage across electrode 102 in response to the same current drive as depicted in FIG. 3A. In the waveform of FIG. 6A, the second phase ($t_2$ 152 to $t_4$ 156) has exactly half its area 162 below zero and half above. In this case, energy is returned early in the second phase (between $t_2$ 152 and $t_3$ 154), and lost late in the second phase (between $t_3$ 154 and $t_4$ 156). Over the whole second phase, no net energy is recovered or lost. That is, the amount of energy burned in the resistive element 104 during the second phase is the same as the amount of energy that had been stored in the capacitance 106. The waveform of FIG. 6B shows a more extreme case, in which at no time during the second phase (between $t_6$ 160 and $t_7$ 161) is energy recovered from the capacitance 106. The differences between the two illustrated waveforms are determined by the relation between the RC product, or respective time constants, of the electrodes, and the pulse duration T/2.

For the waveform of FIG. 6A, no net energy is recovered or lost, and the condition derives from Eq. 5, $$U_2 = I_d^2\left(\frac{RT}{2} - \frac{T^2}{8C}\right) = 0 \qquad \text{Eq. 7}$$
$$RC = \frac{T}{4}$$

For the waveform of FIG. 6B, no energy is recovered at any time, the condition derives from Eqs. 1 and 2, $$V_R = V_C \qquad \text{Eq. 8}$$
$$RC = \frac{T}{2}$$

Thus if the biphasic pulse time T can be made longer than twice the RC time constant of an electrode 102, instantaneous power can be returned from the capacitance 106. If T is made longer than four RC time constants, net energy is recoverable over the second phase (between $t_6$ 160 and $t_7$ 161). Electrodes currently used in retinal implants, for example, have RC time constants that are far less than any expected pulse duration, so energy should be recoverable from the electrodes.

Optimal Drive

Regardless of whether energy can be returned from the capacitance 106 of one or more electrodes 102, the technique described below will approach the minimum level of energy required to drive the electrodes.

In order to store charge (and therefore energy) in the capacitance and then remove it, the charge must be moved through the resistive element 104, and through any resistive element in series between a power supply 164 and one or more electrodes 102.

Power Burned Within the Electrode

The resistive element 104 of the electrodes cannot be removed, so the power burned in it must be minimized. Since a prescribed amount of charge must be driven through the resistive elements in a prescribed pulse time, the only variable is the current waveform used to deliver this charge. The typical current waveform, using a constant current $I_d$ over the pulse duration, as shown in FIG. 3A, is the optimal waveform to minimize power burned in the electrode resistance, given the constraint of delivering a prescribed charge in a fixed time.

A slightly varied current waveform will use more energy to deliver the same charge in the same time. Take for example a current waveform with the current level set slightly below $I_d$, or $I_d-\delta$, for the first phase 110 of the pulse duration, and slightly above $I_d$, or $I_d+\delta$, for the second phase 114. Since power burned in a resistor is $P=I^2R$, the energy burned in the resistance in the optimal, constant-current waveform in one phase is:

$$U_{pot} = I_d^2 \frac{RT}{2} \qquad \text{Eq. 9}$$

The energy used in this example waveform is:

$$U = (I_d + \delta)^2 R \frac{T}{4} + (I_d - \delta)^2 R \frac{T}{4} \qquad \text{Eq. 10}$$

$$U = R\frac{T}{4}(I_d^2 + 2I_d\delta + \delta^2 + I_d^2 - 2I_d\delta + \delta^2)$$

$$U = I_d^2 R \frac{T}{2}\left(1 + \left(\frac{\delta}{I_d}\right)^2\right)$$

The energy used by this example waveform is greater than the energy used by the constant-current waveform of FIG. 3A. Furthermore, it can be shown with variational calculus that the constant-current waveform uses less energy than any other waveform delivering the same charge in the same time, and therefore, that the constant-current waveform burns the least amount of energy possible in the resistance within the electrode.

The resistive elements 104 of electrodes 102 cannot be removed, so the power burned in them must be minimized. The power is minimized, as shown in the previous document, by driving a constant current through the electrodes.

Power Burned Outside the Electrodes

The typical implementation of a constant-current source involves a voltage supply that is higher than the highest voltage reached by the electrodes, with some variable resistive element (usually transistor-based circuitry) in series to control the current. The problem with this approach is that the series resistive element burns power as it supplies charge to the electrode. The present invention solves this problem by removing the series resistance.

If the series resistance is removed, the voltage supply itself must adapt to maintain a constant current. This task is very difficult unless the load impedance is well known, as it is in this case. The load impedance of a variety of tissues can be and has been well characterized. An ideal current driver, with no power dissipation in the source, can be made if the voltage being supplied to the electrodes "tracks" the electrode voltage waveforms shown in FIG. 6A or 6B, that is, if the voltage difference between the capacitance of the electrodes and the voltage source supplying the stimulating energy are limited to a minimum. This keeps the voltage across the resistive portion 104 of the electrodes 102 constant, generating a constant current, the minimum power dissipation in the electrode resistance, and no power dissipation in the supply.

Power Efficient Electrode Supply: First Embodiment

Figure 7:
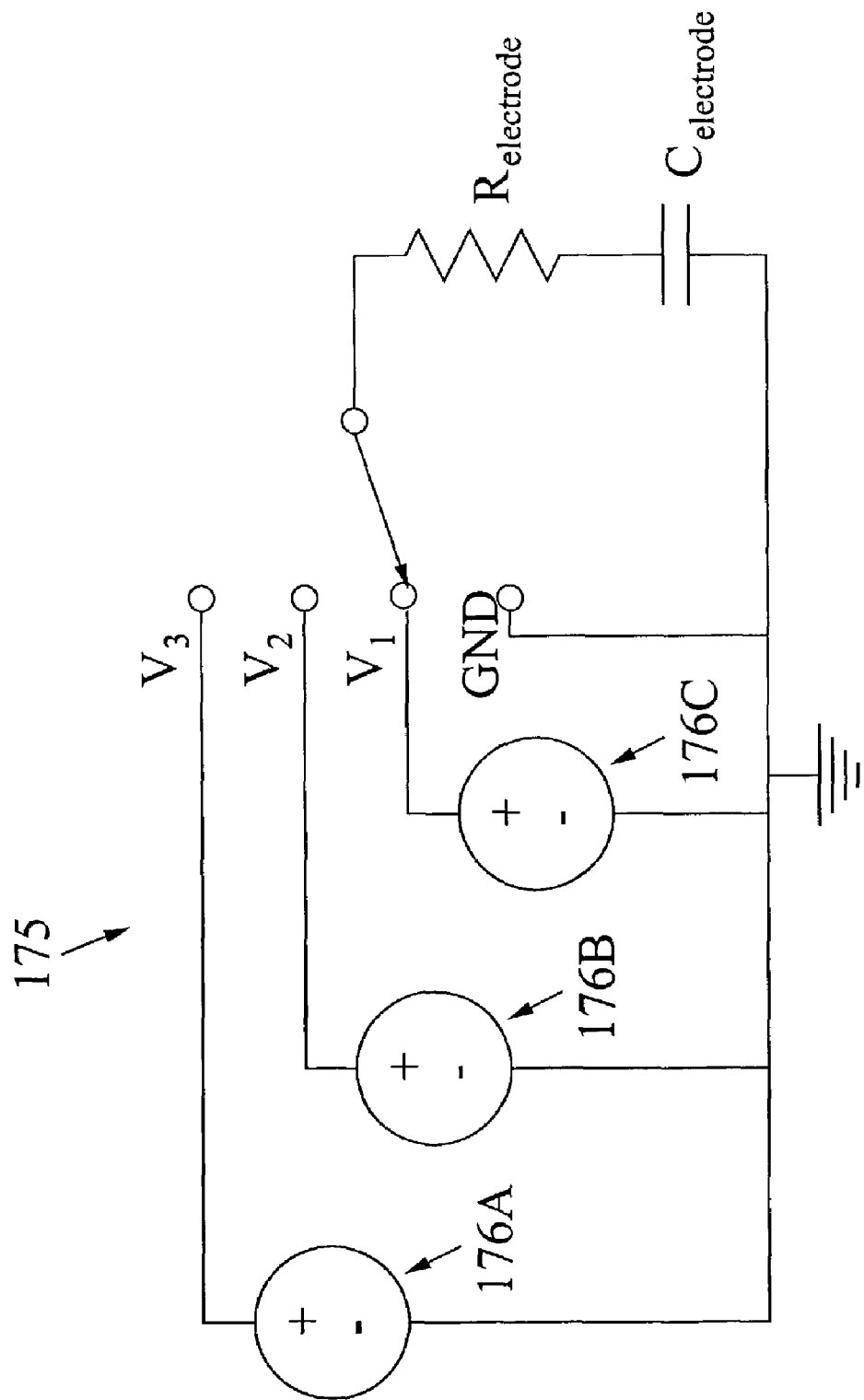
FIG. 7 is an electrical schematic diagram of a first embodiment of a switching supply source in accordance with the present invention.
Figure 8A:
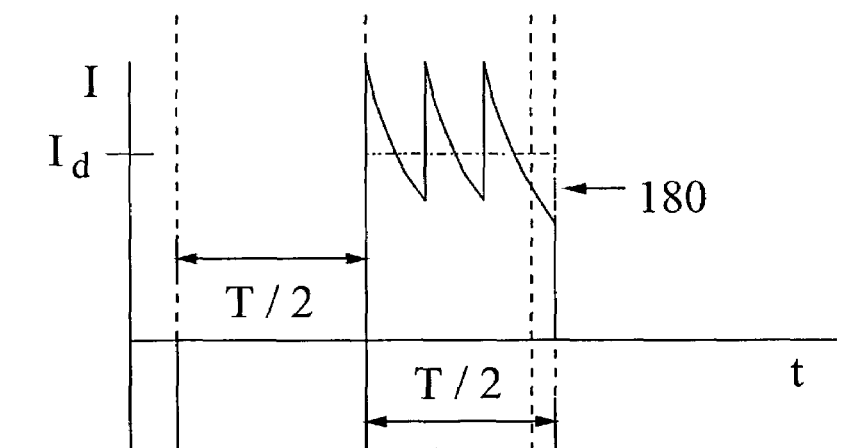
FIGS. 8A, 8B are plots illustrating optimal and realistic current and voltage waveforms across an electrode in accordance with the first embodiment of the switching supply source.
Figure 8B:
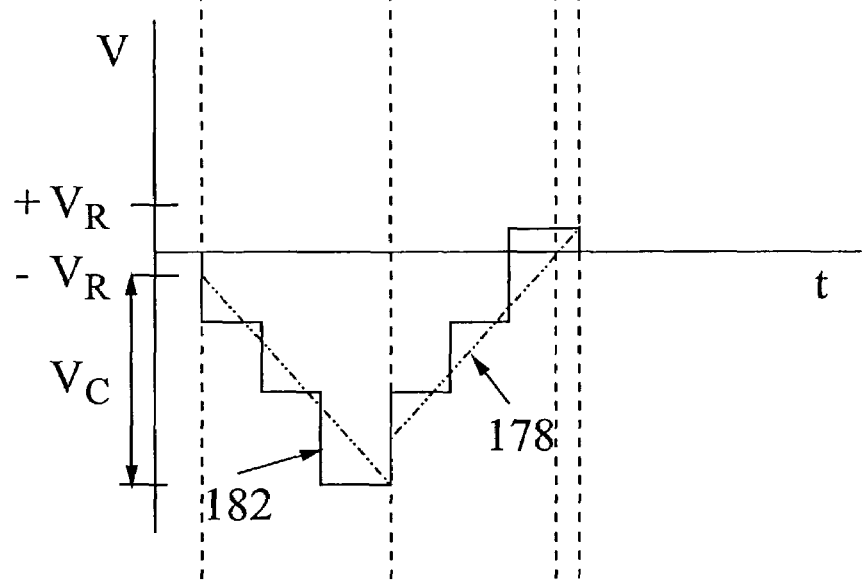

In reality, a voltage supply that follows the step-ramp pattern in FIG. 6A or 6B is very difficult to build. But an approximation to those patterns can be made by switching between a number of different voltage supplies 176A-C, as shown schematically in FIG. 7. A typical implementation for a power efficient voltage supply 175, as shown, might use three voltage sources 176A-C for each phase 110, 114. The total number of voltage sources in that case could be held to four if the middle voltage source 176B were used in both phases. This is shown in the waveforms of FIGS. 8A and 8B, with three negative voltages and one positive voltage. The use of a greater number of voltage levels will yield a closer approximation to the minimum required power, but at a cost of increased system complexity. The dashed lines represent the optimal electrode voltage 178 and optimal current 180 waveforms for minimal power dissipation. One of the solid lines illustrates a four-level voltage approximation waveform 182 of this embodiment, and the resultant electrode current 184.

Power Efficient Electrode Supply: Second Embodiment

Figure 9:
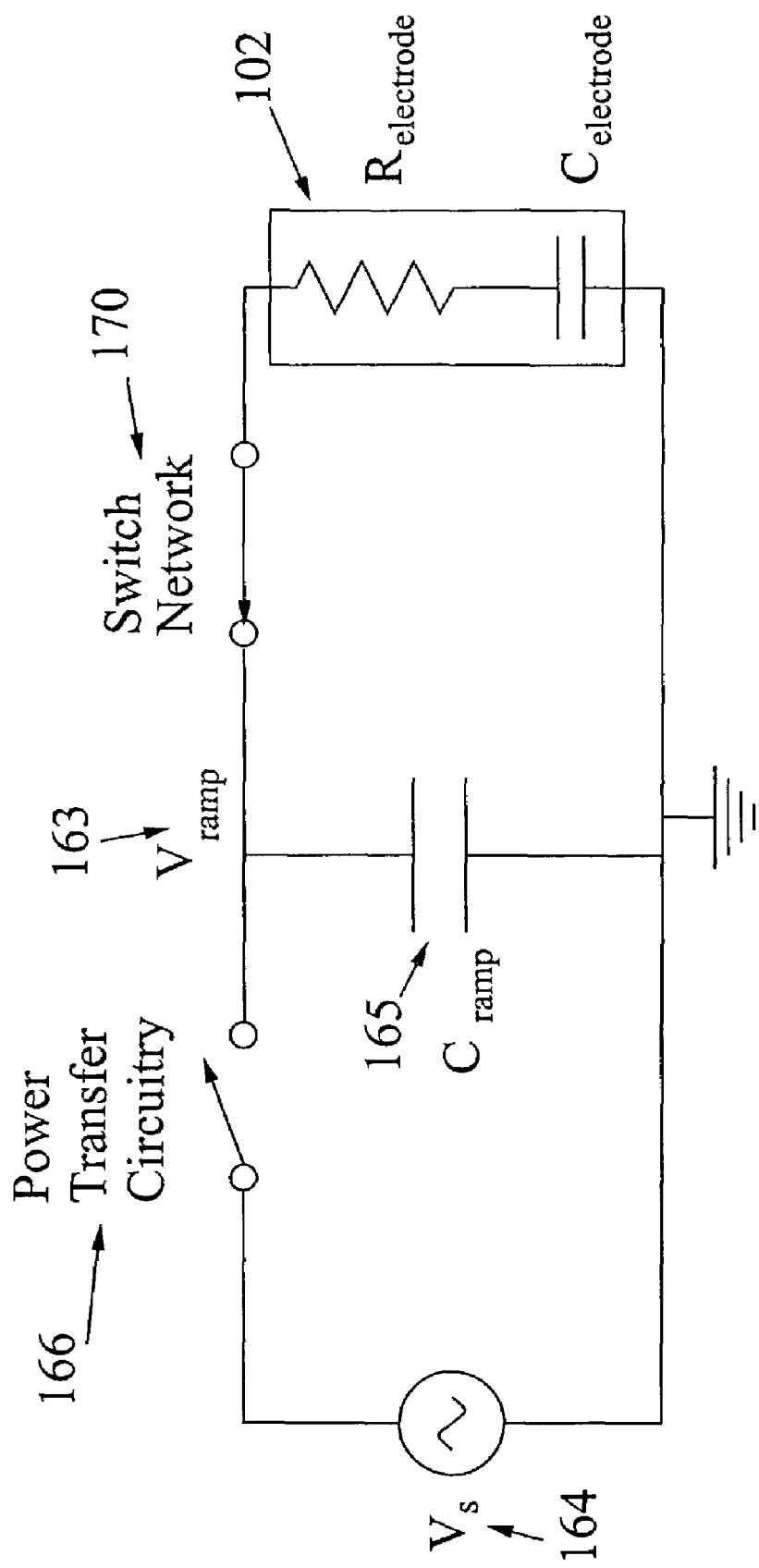
FIG. 9 is an electrical schematic diagram of a second embodiment of a switching supply source in accordance with the present invention.

Another embodiment of a power efficient electrode supply 175 is illustrated in FIG. 9. In this configuration, a ramping voltage 163 may be made available to charge electrode 102 (or multiple electrodes not shown) by driving a constant current from a power supply 164 into a storage capacitor 165 by means of power transfer circuitry 166. Capacitor 165 comprises a portion of an intermediate distribution system (IDS) 168, which is represented in FIG. 1 as a bank of storage capacitors. Storage capacitor 165 will be the only capacitor connected to the electrode being stimulated during a single constant-current phase. Switch network 170 establishes and interrupts connections between the ramping capacitor 165 and the electrodes 102 to be stimulated. Capacitor 165 can be charged to give a pseudo-ramping voltage by power transfer circuitry 166. There will be some ripple in the ramp, but it can be kept small.

Power transfer circuitry 166 and switch network 170 are each depicted as switches in FIG. 9. Switch network 170 in this embodiment connects the one or more electrodes 102 to the storage capacitor 165 for the duration of one phase T/2 of stimulation. Power transfer circuitry 166 switches as the power supply 164 sine wave changes, driving charge onto storage capacitor 165 to achieve the waveform shown in FIG. 10.

This description relates to one phase of biphasic current stimulus. The other phase can be achieved by quickly stepping storage capacitor 165 to a different voltage to represent the step that occurs at time $t_2$ 152 in FIG. 3B, but such a step of voltage on a capacitor cannot be done efficiently. Another way to achieve such a voltage step to start the second current phase 114 is to switch the electrode (s) 102 away from the storage capacitor that has been used, to a different storage capacitor operating at the desired voltage. This second storage capacitor may then be ramped, in the same manner, in the opposite direction to generate the opposite current.

Figure 10:
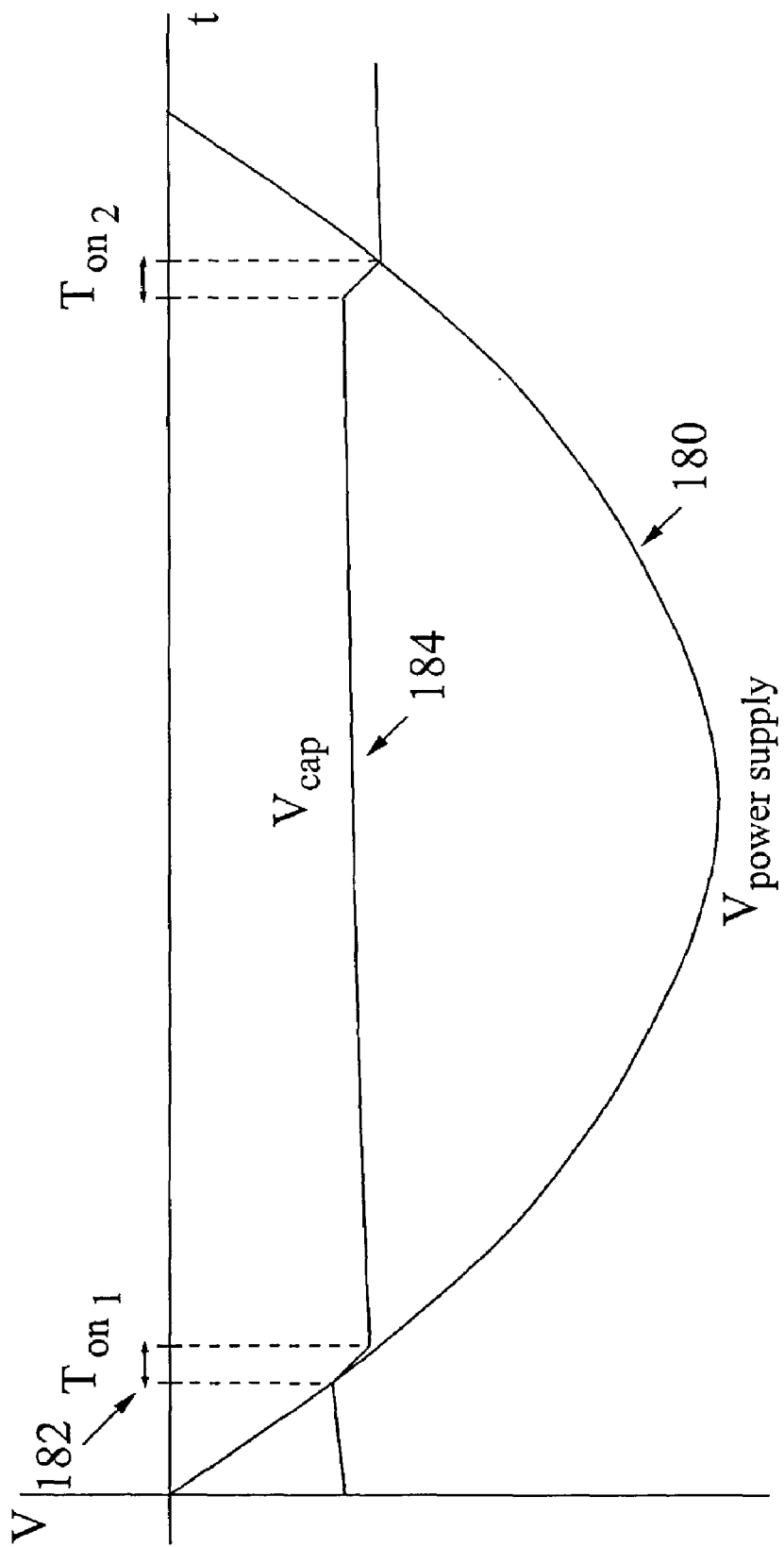
FIG. 10 is a plot illustrating potential switch timing for the second embodiment of the switching supply source.

The power transfer circuit 166 charges the storage capacitor 165 to achieve a ramping waveform, by connecting the capacitor to a sinusoidal power supply 164 with a period much shorter than the pulse width of the stimulus current. FIG. 10 illustrates the timing for half of a sine wave cycle of the power supply voltage 180. Power transfer circuit 166 is turned on at time 182 when the power supply voltage 180 is larger in magnitude than the voltage of the storage capacitor, $V_{cap}$ 184 but close enough to $V_{cap}$ 184 to minimize losses in the power transfer.

Figure 11A:
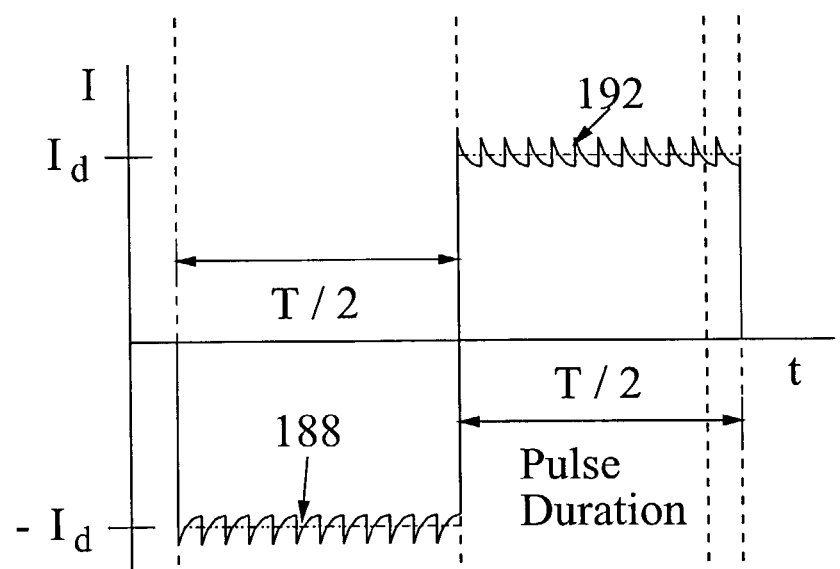
FIGS. 11A, 11B are plots illustrating optimal and realistic current and voltage waveforms across an electrode in accordance with the second embodiment of the switching supply source.
Figure 11B:
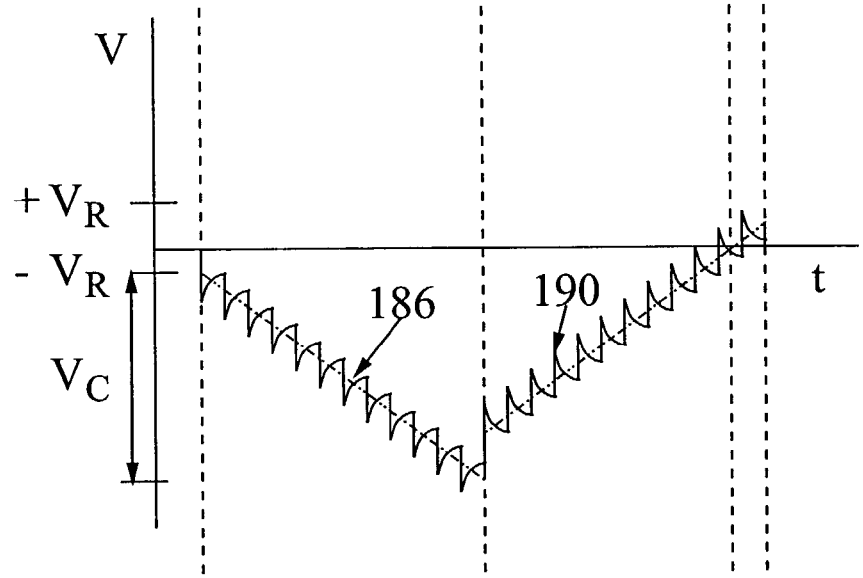

FIGS. 11A and 11B illustrate the ideal and realistic electrode current and voltage waveforms that may be attained employing the circuit described above. The dashed lines represent the optimal electrode voltage 186 and current 188 waveforms for minimal power dissipation. The solid lines illustrate a representation of the voltage 190 and current 192 waveforms utilizing the ramping capacitor solution. In reality, the ripple on the voltage and current waveforms would be much higher frequency, and smaller in magnitude than depicted.

Complete Circuit Implementation

FIG. 1 is a block diagram of a system 100 in accordance with the present invention, including means for efficiently transferring energy and for recovering energy from one or more electrodes 102 following stimulation.

A power supply 164 that receives energy wirelessly, such as in the form of a coupled AC magnetic field, from an external power transmitter 194 is preferable in implanted tissue stimulators, due to the decreased risk of patient infection and increased mobility of the patient. To transmit power to the power supply 164, external power transmitter 194 is placed against the outside of a patient's skin 196 over the implanted tissue stimulator. The ac magnetic fields from the external power transmitter 194 induce ac currents in a secondary coil comprising the power supply 164. Power supply 164 may either be directly connected to the electrodes 102 or to power transfer circuitry 166 that rectifies the ac current to produce dc current for charging the one or more voltage sources 198 in IDS 168 to their desired voltages.

The voltage sources 198 are preferably implemented using storage capacitors, as previously described. The voltage sources 198 are maintained at their prescribed voltage level by power transfer circuitry 166, charging from whatever power supply 164 is being used for the implant (battery, RF coil, etc.).

FIG. 1 shows a block diagram of a multi-source system, with a bank of capacitors 198 forming part of IDS 168 charged from power supply 164, and driving the electrodes 102 as described above, through switch network 170. Switching control 174 receives whatever data is required to determine which electrodes need to be driven, and the switching network 170 connects each electrode to an appropriate sequence among voltage sources 198 to create the waveforms portrayed in FIGS. 11A and 11B.

The power transfer circuitry 166 may be comprised of a synchronous switching rectifier for repeatedly causing a rectified ac voltage to accumulate across the voltage sources 198 in a step-wise fashion.

The charging of the voltage sources 198 may occur according to a predetermined timing or pulse-counting routine. Alternatively, power transfer circuitry 166 may monitor the voltage difference(s) between the power supply 164 and the voltage(s) of the one or more voltage sources 198, perhaps through the use of a voltage comparator. With this knowledge, power transfer circuitry 166 may determine the appropriate connection sequence between the power supply 164 and the voltage sources 198.

Figure 12:
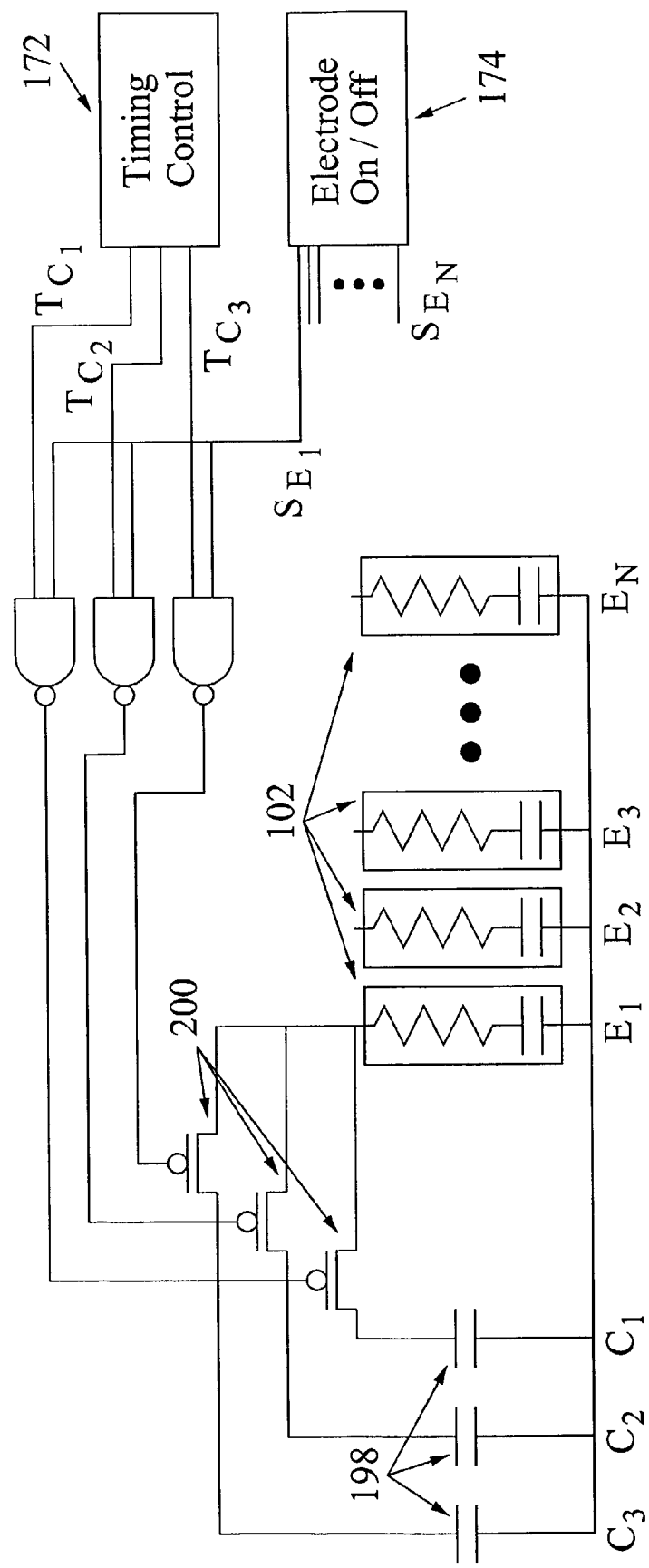
FIG. 12 is an electrical schematic diagram illustrating an embodiment of a switching network in accordance with the present invention.

FIG. 12 is a functional block diagram of a portion of the present system that illustrates switching control between a plurality of voltage sources 198 and one or more electrodes 102. The voltage sources 198 of the IDS 168 are connected to a plurality of switches 200 that will typically be implemented using solid state switching devices as are known in the art, and whose operation is controlled jointly by digital timing control 172 and electrode switching control 174. In the circuit shown, CMOS Field effect transistors serve as the switches 200 for individually coupling one or more of the storage capacitors to one or more of the electrodes 102 based on signals asserted by digital timing control 172 and electrode switching control 174. Although timing intervals may determine the operation of the switches 200, alternatively the connections can be made in response to monitored between the various voltage sources 198 and the one or more electrodes 102 are determined either open-loop by the timing circuitry or by a more complicated feedback system measuring either electrode voltage or supplied current.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

We claim:

1. A system for power recovery in a tissue stimulator, comprising:
   one or more tissue stimulating electrodes, each having a capacitance; and
   means for recovering post-stimulation energy from the electrodes and further comprising:
   a power supply; and
   power transfer circuitry coupled to the power supply and the electrodes that provides energy to the electrodes directly from the power supply while limiting voltage differences between the power supply and the capacitance of the electrodes to which the power supply is to be connected, wherein the power transfer circuitry further comprises a synchronous switching rectifier for directly recovering power from the one or more storage capacitors, wherein the power transfer circuitry is responsive to timing intervals from a timing control unit.

2. A system for power-recovery in a tissue stimulator, comprising:
   one or more tissue stimulating electrodes, each having a capacitance; and
   means for recovering post-stimulation energy from the electrodes and further comprising:
   a power supply;
   an intermediate distribution network including one or more storage capacitors;

a switching network coupled to the one or more electrodes and the intermediate distribution system, that provides energy to the electrodes from the one or more storage capacitors while limiting voltage differences between the storage capacitors and the capacitance of the electrodes to which the storage capacitors are to be connected; and power transfer circuitry coupled to the power supply and the intermediate distribution system, that provides energy to the storage capacitors from the power supply while limiting voltage differences between to power supply and the storage capacitors to which the power supply is to be connected, wherein the power transfer circuitry further comprises a synchronous switching rectifier for directly recovering power from the one or more storage capacitors wherein the power transfer circuitry is responsive to timing intervals, from a timing control unit.

3. A system for power-recovery in a tissue stimulator, comprising:

a power supply;

an intermediate distribution system including one or more storage capacitors;

power transfer circuitry, coupled to the power supply and the intermediate distribution system that recovers energy from the storage capacitors to the power supply while limiting voltage differences between the power supply and the storage capacitors to which the power supply is to be connected;

one or more tissue stimulating electrodes, each having a capacitance; and a switching network, coupled to the one or more electrodes and the intermediate distribution system, that provides sequential connections for the one or more storage capacitors to one or more of the electrodes while limiting voltage differences between the storage capacitors and the capacitances of the one or more electrodes to which the one or more storage capacitors are to be connected wherein the power transfer circuitry further comprises a synchronous switching rectifier for directly recovering power from the one or more storage capacitors wherein the power transfer circuitry is responsive to timing intervals from a timing control unit.

* * * * *